United States Patent [19]

Tamir

[11] Patent Number: 5,141,872

[45] Date of Patent: Aug. 25, 1992

[54] METHOD FOR DETERMINATION OF LDL-CHOLESTEROL

[76] Inventor: Ilana Tamir, 102 N. Oak Ave., Pasadena, Cal. 91107

[21] Appl. No.: 466,788

[22] Filed: Jan. 18, 1990

[30] Foreign Application Priority Data

Jan. 31, 1989 [IL] Israel .......................................... 89123

[51] Int. Cl.$^5$ ..................... G01N 33/92; G01N 33/49; G01N 1/18
[52] U.S. Cl. ......................................... 436/71; 436/86; 436/164; 436/175; 436/178
[58] Field of Search .................... 436/71, 86, 164, 175, 436/178

[56] References Cited

U.S. PATENT DOCUMENTS 4,883,765 11/1989 Tamir et al. .......................... 436/71

Primary Examiner—James C. Housel
Assistant Examiner—Arlen Soderquist
Attorney, Agent, or Firm—Sandra M. Kotin

[57] ABSTRACT

A method for the direct quantitative determination of LDL-cholesterol in a sample of blood plasma which involves selective adsorption of lipoproteins on silica, removal of high density lipoproteins by incubation in a suitable detergent solution, extraction of the remaining LDL-cholesterol by another detergent and determination of the LDL-cholesterol by spectrophotometric analysis.

12 Claims, 1 Drawing Sheet

METHOD FOR DETERMINATION OF LDL-CHOLESTEROL

The present invention relates to a method for direct quantitative determination of low density lipoprotein cholesterol (hereinafter referred to as LDL-cholesterol) in blood plasma.

More specifically the present invention relates to a method which enables us to make a direct quantitative determination of LDL-cholesterol in a commercially available automated clinical chemistry analyzer or any other spectroscopic device by prior specific adsorptions and desorptions of blood plasma from an active surface.

Blood plasma contains about 10 percent dissolved solids, of which about 70 percent consists of plasma proteins. Among major plasma proteins are very low density lipoproteins (VLDL), low density lipoproteins (LDL), and high density lipoproteins (HDL). Recent publications emphasize a positive statistical correlation between the incidence of coronary heart disease and high levels of low density lipoproteins, and in deciding upon therapy, it is considered to be the key parameter for cholesterol reducing therapy (Clin. Chem, 34/1, 193, 1988). This opinion is supported by Dr. H. K. Naito in Clin. Chem. 34/2, 444 (1988).

It is of great value and importance to measure the LDL-cholesterol parameter directly rather than use an empirical limited equation (The Friedewald equation, Friedewald W. T., Levy, R. I., Freidrickson D. S., Clin. Chem. 18, 499, 1972), as is done today using the data obtained by determination of total cholesterol (TC), triglycerides (TG) and high density lipoproteins (HDL).

The use of the empirically limited Friedewald equation in order to calculate the LDL-cholesterol level in blood plasma as is done today demands prior to calculation three separate determinations on an analyzer-of total cholesterol, triglycerides, and high density lipoproteins. This is a long and complex procedure which is vulnerable to error in any of the three determinations noted above, and any of these errors leads to an error in the calculated determinations of the LDL-cholesterol. In addition, errors may arise in the stage of calculation. The Friedewald equation is limited to TG values below 400 mg/dl; and even in this range its parametrization is questionable (estimation of LDL by the Friedewald formula and by electroporesis compared. R. S. Niedlbala and K. G. Schray Clin. Chem. Vol. 31, 1762, 1985).

There is a great need for a simple and rapid method that can permit a direct quantitative measurement of LDL-cholesterol with a clinical chemistry analyzer. (Report of the National Cholesterol Education Program by the National Heart, Lung and Blood Institute—The adult cholesterol treatment recommendation [1987] Clin. Chem. Feb 1988; Policy Recommendations for Prevention of Coronary Heart Disease Position—Paper of the Israeli Society for Research on Arteriosclerosis, published in Harefua Medical Journal No. 6, Volume 314, 1988; Lowering LDL-cholesterol NIH consensus development conference statement 1985; Arteriosclerosis 5, 404, 1985). It is the object of the present invention to fulfill this need and provide a facile method which can permit such a direct measurement of LDL-cholesterol in blood plasma with an analyzer which is on the market (e.g. Impact 400).

The present invention provides a method for direct quantitative determination of LDL-cholesterol in a sample of blood plasma comprising the following steps in which:

(a) a sample of blood plasma is applied to particulate silica capable of selectively adsorbing the lipoproteins from a plasma sample;
(b) incubating said silica in an incubation chamber having a water-saturated atmosphere;
(c) separating the silica from the non-adsorbed components;
(d) washing said silica with water;
(e) incubating said silica in appropriate detergent;
(f) separating said silica from the detergent;
(g) extracting LDL-cholesterol from said silica by an additional step wherein the high density lipoprotein fraction had already been removed; and
(h) direct determination of the LDL-cholesterol with a clinical chemistry analyzer.

Figure 1:
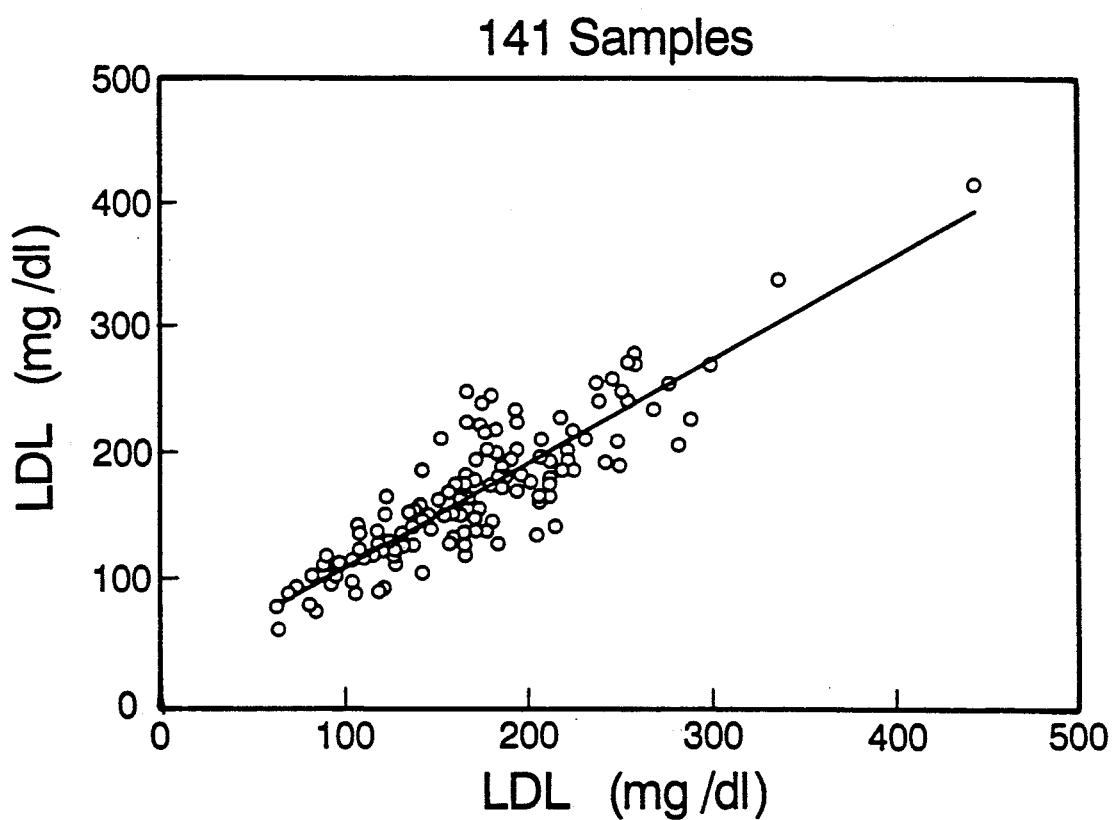
FIG. 1 shows a correlation between results obtained by the direct determination of LDL-cholesterol of the present invention and those obtained by a conventional indirect determination method.

According to the present method the preferred surface active compound which is capable of selectively adsorbing the lipoproteins from a plasma sample is fumed silica (pure silicon dioxide with specific size of particles). More specifically—the commercially available fumed silica (e.g. "Cabosil"-Cabbot Company; "Aerosil"-Degussa company). The silica can be coated on any inert solid carrier (e.g. glass, paper, plastic polymer etc.) in any shape, (e.g. plate, rod or ball).

The selective adsorption of lipoproteins by fumed silica, and the removal of lipoproteins from human plasma was described in the literature, (e.g. C. B. Glaser et al., "The Isolation of Alpha-1-Protease Inhibitor by a Unique Procedure Designed for Industrial Application" Anal. Biochem. 124, 364–371, 1982) but there was no description of methods for selective removal from said silica and direct determination of LDL-cholesterol.

The detergent concentration in the extraction solutions and the length of the incubation period were such as would ensure complete removal of the corresponding lipoprotein fractions. The detergents solutions are solutions capable of extracting the specific fractions, e.g.: Polyoxy ethylene$_{(20)}$ sorbitan-monostearate (commercially available as "Tween 60") to selectively extract the HDL-cholesterol and, Sodium dodecyl sulfate (SDS), and Ethoxlated phenol-p-isooctyl of the formula

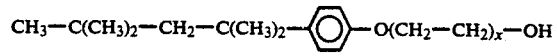

$$CH_3-C(CH_3)_2-CH_2-C(CH_3)_2-\phantom{}\!\!\bigcirc\!\!\phantom{}-O(CH_2-CH_2)_x-OH$$

wherein x is 10 on the average (commercially available as "Triton X-100"—Rohan and Hass) to remove the remaining LDL-cholesterol for direct determination.

The interaction of the lipoprotein with silica is strong, but the leaching process of the adsorbed lipoproteins is enhanced by providing a water-saturated atmosphere in the incubation chamber. This was accomplished by placing a shallow pan of water in the bottom of the incubation chamber.

As a specific example the present method comprises the following steps:

(a) a sample of 5 μL. of blood plasma is applied to a fumed silica coated on a plate or a rod of any solid inert material (hereinafter referred to as "the device");
(b) incubating the device for 10 minutes in an incubation chamber having a water-saturated atmosphere (100% humidity);
(c) rinsing the device with tap water;
(d) incubating the device for 20 minutes at 37° C. in 750 μL. of the appropriate detergent;
(e) removing the device;
(f) obtaining the extraction solution of the LDL test by an additional step performed on the device from which the HDL fraction had already been removed by incubating it for 15 minutes at 37° C. in the appropriate detergent;
(g) direct quantitative determination of LDL-cholesterol in a clinical chemistry analyzer (e.g. Ciba Corning Diagnostics Instrument Impact 400).
  (1) Add 0.4 mL. of cholesterol reagent to 100 μL. of the corresponding extraction solution;
  (2) Incubate for 10 minutes;
  (3) Read optical density of 500 nm and calculate the corresponding concentration with respect to the appropriate standard.

The preferred detergent for stage (d) is Tween-60 (preferred 1%).

The preferred detergents for stage (f) are Triton X-100 (preferred 0.64%) or sodium dodecyl sulphate (preferred 0.1%).

The above example is given only for the purpose of illustrating the present invention.

The invention is further illustrated by means of the following non-limiting examples and tables.

Example 1

Precision Study

Three commercial control sera were used, in the low, normal and high cholesterol ranges. Control serum 1 was a human serum control—normal Mytrol (TC=170 mg/dl). Control serum 2 was a very high LDL and total cholesterol (TC) level from an Israeli hospital patient. Control serum 3 was monitrol II E (TC=116 mg/dl).

The above mentioned control sera were assayed, using 10 replicates, for a period of at least 5 days. This meant utilization of 10 portions of the same control serum for total cholesterol (hereinafter referred to as TC) and triglycerides (hereinafter referred to as TG) on the analyzer, and ten replicates were treated for high density lipoprotein determination. The results from the precision studies are summarised in Table 1.

TABLE 1

Precision Studies

| Cont | Date | \multicolumn{4}{c}{The Conventional Indirect Method-CCD} | The method According to the current invention |
|---|---|---|---|---|---|---|

| Cont | Date | TC mg/dl | | TG mg/dl | | HDL mg/dl | | LDL-CAL mg/dl | | LDL mg/dl | |
|---|---|---|---|---|---|---|---|---|---|---|---|
| | | 189.9 | (2.5) | 274.6 | (3.3) | 12.0 | (5.7) | 123.0 | | 115.6 | (14.8) |
| | | 172.6 | (26.6) | 277.2 | (13.9) | 20.3 | (0.8) | 96.9 | | 104.8 | (10.0) |
| | | 191.9 | (6.0) | 267.3 | (4.9) | 19.2 | (0.6) | 119.2 | | 105.8 | (17.2) |
| | | 201.2 | (1.0) | 274.6 | (2.2) | 18.7 | (0.5) | 127.6 | | 104.2 | (19.8) |
| | | 193.4 | (4.5) | 262.5 | (5.1) | 18.0 | (0.6) | 122.9 | | 110.5 | (15.8) |
| | | 168.0 | (1.7) | 251.0 | (4.0) | 18.6 | (0.5) | 99.2 | | 119.7 | (11.3) |
| +SD | | 188.1+ | (12.9) | 266.7+ | (9.6) | 18.2+ | (2.9) | 115.5+ | (13.0) | 108.2+ | (7.7) |
| | | 458.8 | (2.0) | 59.0 | (2.8) | 12.8 | (5.8) | 434.2 | | 400.6 | (32.6) |
| | | 469.8 | (4.3) | 57.3 | (1.3) | 18.4 | (1.0) | 439.9 | | 360.2 | (15.1) |
| | | 483.1 | (15.6) | 62.0 | (0.9) | 17.5 | (0.5) | 453.2 | | 382.4 | (19.1) |
| | | 469.7 | (4.5) | 52.9 | (0.7) | 17.1 | (0.4) | 442.0 | | 373.4 | (18.3) |
| +SD | | 473.4+ | (11.0) | 57.8+ | (3.3) | 16.9+ | (2.4) | 445.0+ | (9.1) | 367.9+ | (29.0) |
| | | 117.2 | (1.6) | 183.9 | (1.8) | 11.2 | (5.7) | 69.2 | | 86.8 | (8.9) |
| | | 117.0 | (5.1) | 187.2 | (1.8) | 18.6 | (0.6) | 61.0 | | 77.7 | (4.7) |
| | | 123.4 | (0.9) | 161.0 | (2.4) | 18.4 | (0.7) | 72.8 | | 83.8 | (4.0) |
| | | 121.2 | (3.0) | 162.2 | (1.2) | 17.1 | (0.5) | 71.6 | | 71.3 | (10.1) |
| | | 104.6 | (1.8) | 157.9 | (0.6) | 17.8 | (0.6) | 55.2 | | 86.4 | (7.2) |
| +SD | | 118.7+ | (8.2) | 173.7+ | (14.7) | 17.1+ | (3.0) | 66.9+ | (10.7) | 79.3+ | (7.6) |

Cont = Control
() = 1 standard deviation in mg/dl.
LDL-CAL = Calculated LDL-cholesterol (Friedewald equation)

Table 2 shows the averaged values for intra-assay and inter-assay precision in the direct measurement of LDL-cholesterol according to the present invention.

TABLE 2

LDL-cholesterol: Intra-assay - Inter-assay Precision

| | Intra-assay | LDL-CAL Inter-assay |
|---|---|---|
| Control 1 | 14.8 | 13.0 |
| Control 2 | 23.4 | 9.1 |
| Control 3 | 8.9 | 10.9 |

The results of the direct determination of LDL-cholesterol according to the present invention for control sera 1 and 3 are very similar to those for LDL-cholesterol concentration calculated using the Friedewald equation (hereinafter referred to as LDL-CAL).

The data for control serum 2 differ in the LDL-CAL and the present method. This may be due to two factors: 1) The abnormally high levels of LDL and TC in this sample and 2) The use of the Friedewald equation for calculation of LDL which, for such an abnormal sample, is questionable.

Example 2

Comparison Study 151 samples were assayed in duplicate on the Impact-400 analyzer. Most of the samples were obtained from patients with various types of hyperlipoproteinemia—I, IIa, IIB, IV and V. 141 samples were used in analysis of LDL-cholesterol results (see Table 3), 10 samples were omitted from the comparison (see Table 4) for the following reasons. Five samples had triglyceride levels above 400 mg/dl, and the Friedewald equation is not suitable for calculating LDL with high TG. Four samples had very high LDL and TG levels which seemed to be beyond the present capacity of the device. One sample (No. 134) had low cholesterol (80 mg/dl) and TG (294 mg/dl) levels, resulting in a LDL-CAL value of 10 mg/dl, which was considered unrealistic.

FIG. 1 shows a correlation between results obtained by means of the direct determination of LDL-cholesterol according to the present invention and those obtained by the conventional indirect determination method. The latter method requires determination of TC, TG, and HDL and calculation of the LDL-cholesterol by use of the Friedewald equation. A very positive regression was obtained, with a slope of 0.82, an intercept of 28.6 mg/dl and a correlation coefficient of 0.88.

All the above results indicate that precision and accuracy are improved by the present invention relative to the current standard indirect method of calculating this value using the Friedewald equation.

TABLE 3

AVERAGE DATA FOR EVERY SAMPLE (LDL CORRELATION)

| Sample no | TG mg/dl | TC mg/dl | HDL mg/dl | LDL mg/dl | LDL-CAL. mg/dl |
|---|---|---|---|---|---|
| 1.0 | 144.5 | 322.3 | 46.0 | 260.0 | 247.4 |
| 2.0 | 159.0 | 269.2 | 61.3 | 240.5 | 176.1 |
| 3.0 | 162.0 | 269.4 | 56.2 | 246.2 | 180.8 |
| 4.0 | 85.0 | 254.6 | 61.2 | 217.0 | 176.5 |
| 5.0 | 166.0 | 233.3 | 46.5 | 212.1 | 153.6 |
| 6.0 | 123.0 | 267.8 | 61.1 | 219.5 | 182.2 |
| 7.0 | 112.5 | 263.8 | 73.8 | 225.4 | 167.6 |
| 8.0 | 115.5 | 257.7 | 40.1 | 225.3 | 194.6 |
| 9.0 | 155.0 | 263.5 | 38.0 | 204.0 | 194.5 |
| 10.0 | 122.5 | 220.4 | 52.6 | 187.5 | 143.3 |
| 11.0 | 96.5 | 243.9 | 46.4 | 203.5 | 178.2 |
| 12.0 | 87.5 | 349.9 | 73.2 | 271.7 | 259.2 |
| 13.0 | 108.5 | 327.0 | 111.7 | 234.8 | 193.6 |
| 14.0 | 103.5 | 331.3 | 54.4 | 273.8 | 256.3 |
| 15.0 | 92.5 | 319.5 | 46.9 | 242.9 | 254.2 |
| 16.0 | 141.5 | 297.5 | 50.1 | 228.9 | 219.1 |
| 17.0 | 129.0 | 324.1 | 38.8 | 279.9 | 259.6 |
| 18.0 | 373.0 | 319.9 | 28.1 | 228.4 | 217.3 |
| 19.0 | 301.0 | 460.4 | 62.6 | 338.4 | 337.6 |
| 20.0 | 272.5 | 322.6 | 48.6 | 187.8 | 219.6 |
| 22.0 | 62.0 | 471.0 | 13.4 | 414.8 | 445.2 |
| 23.0 | 269.5 | 328.7 | 25.3 | 210.1 | 249.5 |
| 24.0 | 231.0 | 291.3 | 59.7 | 185.9 | 185.4 |
| 25.0 | 308.5 | 267.7 | 26.4 | 176.2 | 179.6 |
| 26.0 | 243.5 | 275.9 | 40.6 | 174.2 | 186.7 |
| 27.0 | 326.5 | 385.0 | 42.4 | 255.5 | 277.3 |
| 28.0 | 290.5 | 296.7 | 30.6 | 198.1 | 208.0 |
| 29.0 | 517.0 | 265.6 | 39.0 | 167.4 | 123.2 |
| 30.0 | 356.5 | 293.0 | 33.7 | 181.8 | 188.0 |
| 31.0 | 397.5 | 382.2 | 33.5 | 235.5 | 269.2 |
| 32.0 | 250.0 | 329.8 | 28.4 | 191.2 | 251.4 |
| 33.0 | 224.5 | 231.8 | 44.7 | 160.6 | 142.2 |
| 34.0 | 325.0 | 261.4 | 29.4 | 183.5 | 167.0 |
| 35.0 | 336.5 | 194.2 | 36.6 | 119.7 | 90.3 |
| 36.0 | 236.5 | 252.1 | 43.1 | 177.3 | 161.7 |
| 38.0 | 455.0 | 252.8 | 24.3 | 143.4 | 137.5 |
| 39.0 | 331.5 | 298.3 | 40.6 | 196.1 | 191.5 |
| 40.0 | 329.5 | 217.7 | 29.7 | 152.8 | 122.1 |
| 41.0 | 276.0 | 262.1 | 43.5 | 165.3 | 163.4 |
| 42.0 | 258.0 | 302.5 | 28.4 | 201.5 | 222.5 |
| 43.0 | 150.5 | 264.6 | 27.5 | 164.8 | 207.0 |
| 44.0 | 101.0 | 331.6 | 88.5 | 193.9 | 223.0 |
| 45.0 | 153.5 | 267.9 | 49.4 | 181.7 | 187.8 |
| 46.0 | 155.0 | 320.6 | 50.1 | 241.1 | 239.6 |
| 47.0 | 100.5 | 243.3 | 59.7 | 153.1 | 163.5 |
| 48.0 | 79.0 | 228.6 | 63.9 | 145.5 | 176.8 |
| 49.0 | 102.5 | 242.4 | 40.4 | 135.3 | 159.8 |
| 50.0 | 110.0 | 323.1 | 51.1 | 210.7 | 226.0 |
| 51.0 | 266.0 | 309.5 | 39.3 | 170.2 | 157.9 |
| 52.0 | 153.0 | 311.7 | 46.8 | 210.6 | 207.5 |
| 53.0 | 163.0 | 215.8 | 38.6 | 131.7 | 129.3 |
| 54.0 | 124.5 | 244.9 | 55.4 | 140.6 | 170.8 |
| 55.0 | 138.5 | 176.3 | 37.5 | 112.6 | 90.1 |
| 56.0 | 169.0 | 313.3 | 45.8 | 196.2 | 212.6 |
| 57.0 | 380.5 | 261.0 | 35.0 | 152.6 | 145.5 |
| 58.0 | 133.0 | 266.4 | 39.2 | 182.2 | 212.7 |
| 59.0 | 65.5 | 228.0 | 40.7 | 139.1 | 178.1 |
| 60.0 | 235.5 | 286.0 | 62.5 | 164.7 | 151.9 |
| 61.0 | 100.5 | 208.4 | 58.6 | 141.5 | 147.1 |
| 62.0 | 175.5 | 362.0 | 29.4 | 271.8 | 300.4 |
| 63.0 | 113.5 | 230.4 | 25.9 | 148.1 | 181.2 |
| 64.0 | 176.0 | 387.3 | 46.2 | 255.7 | 238.3 |
| 65.0 | 117.0 | 245.7 | 33.4 | 164.1 | 164.3 |
| 66.0 | 72.0 | 208.1 | 68.0 | 129.2 | 118.0 |
| 67.0 | 107.5 | 295.9 | 53.7 | 200.5 | 183.4 |
| 68.0 | 111.5 | 238.3 | 52.3 | 184.2 | 196.7 |
| 69.0 | 151.0 | 259.1 | 30.8 | 167.1 | 168.2 |
| 70.0 | 178.5 | 339.9 | 45.9 | 248.8 | 167.6 |
| 71.0 | 176.0 | 280.7 | 30.0 | 193.2 | 243.1 |
| 72.0 | 83.0 | 141.9 | 44.3 | 81.4 | 80.2 |
| 73.0 | 107.5 | 276.2 | 42.8 | 169.3 | 211.9 |
| 74.0 | 65.5 | 195.2 | 54.2 | 112.4 | 127.9 |
| 75.0 | 48.0 | 224.0 | 76.0 | 128.3 | 138.4 |
| 76.0 | 86.5 | 240.9 | 39.4 | 129.1 | 184.2 |
| 77.0 | 152.5 | 255.9 | 40.5 | 184.0 | 184.9 |
| 78.0 | 150.5 | 142.6 | 27.6 | 75.5 | 84.9 |
| 79.0 | 195.0 | 192.8 | 31.7 | 94.4 | 122.2 |
| 80.0 | 111.5 | 353.3 | 48.9 | 207.8 | 282.1 |
| 81.0 | 143.5 | 241.3 | 41.0 | 149.9 | 171.6 |
| 82.0 | 75.5 | 221.9 | 41.2 | 119.7 | 165.6 |
| 83.0 | 101.5 | 296.5 | 60.3 | 197.9 | 215.9 |
| 84.0 | 293.0 | 318.4 | 34.1 | 187.6 | 225.7 |
| 85.0 | 156.5 | 190.4 | 32.5 | 122.2 | 126.6 |
| 86.0 | 66.5 | 188.7 | 56.1 | 92.8 | 119.4 |
| 87.0 | 156.5 | 200.1 | 26.0 | 105.8 | 142.8 |
| 89.0 | 62.0 | 180.1 | 47.0 | 93.2 | 120.7 |
| 90.0 | 80.5 | 127.5 | 47.1 | 61.4 | 64.3 |
| 91.0 | 257.0 | 311.1 | 44.8 | 144.1 | 214.9 |
| 92.0 | 137.5 | 279.1 | 44.8 | 167.4 | 206.8 |
| 95.0 | 118.0 | 225.2 | 35.9 | 128.7 | 165.8 |
| 96.0 | 118.5 | 164.8 | 34.9 | 89.5 | 106.2 |
| 97.0 | 311.0 | 332.8 | 47.0 | 194.8 | 223.6 |
| 99.0 | 230.0 | 176.9 | 19.7 | 118.9 | 111.2 |
| 100.0 | 375.0 | 319.3 | 11.9 | 211.0 | 232.4 |
| 101.0 | 60.5 | 179.3 | 43.3 | 130.2 | 123.9 |
| 102.0 | 314.0 | 367.0 | 14.8 | 227.8 | 289.4 |
| 103.0 | 112.0 | 170.8 | 36.3 | 118.4 | 112.1 |
| 104.0 | 81.0 | 220.1 | 67.7 | 155.2 | 136.2 |
| 105.0 | 165.0 | 302.9 | 44.8 | 219.0 | 225.1 |
| 106.0 | 289.0 | 282.6 | 38.0 | 190.3 | 186.8 |
| 107.0 | 45.0 | 150.9 | 59.4 | 103.4 | 82.5 |
| 108.0 | 100.5 | 203.2 | 27.5 | 152.6 | 155.6 |
| 109.0 | 209.0 | 163.5 | 28.9 | 112.7 | 92.8 |
| 110.0 | 174.0 | 237.2 | 36.0 | 139.5 | 166.4 |
| 111.0 | 137.5 | 233.7 | 46.5 | 176.5 | 159.8 |
| 112.0 | 74.0 | 239.2 | 57.9 | 158.1 | 166.6 |
| 113.0 | 219.5 | 259.4 | 43.9 | 180.3 | 171.6 |
| 114.0 | 136.5 | 224.7 | 36.4 | 153.5 | 161.0 |
| 115.0 | 95.0 | 266.3 | 52.6 | 172.5 | 194.8 |
| 116.0 | 107.0 | 223.4 | 45.1 | 129.9 | 157.0 |
| 117.0 | 246.5 | 227.3 | 40.3 | 156.9 | 137.7 |
| 118.0 | 67.5 | 167.1 | 57.7 | 102.3 | 95.9 |
| 119.0 | 99.5 | 286.3 | 64.0 | 178.9 | 202.4 |
| 120.0 | 93.5 | 196.5 | 47.1 | 128.1 | 130.8 |
| 121.0 | 150.5 | 161.1 | 38.2 | 97.7 | 92.8 |
| 122.0 | 100.0 | 216.4 | 48.6 | 141.8 | 147.8 |
| 124.0 | 94.5 | 233.0 | 40.0 | 222.6 | 174.1 |
| 125.0 | 214.5 | 200.2 | 26.1 | 138.9 | 131.2 |
| 127.0 | 222.0 | 283.9 | 26.9 | 175.4 | 212.6 |
| 128.0 | 158.5 | 231.1 | 41.2 | 132.5 | 158.3 |
| 129.0 | 249.0 | 194.9 | 37.4 | 144.1 | 107.8 |
| 130.0 | 263.5 | 202.9 | 41.6 | 138.2 | 108.6 |
| 131.0 | 336.0 | 240.0 | 36.5 | 155.0 | 136.3 |
| 132.0 | 279.0 | 192.5 | 28.2 | 126.2 | 108.5 |
| 133.0 | 106.5 | 190.2 | 50.6 | 140.2 | 118.4 |
| 135.0 | 68.0 | 194.1 | 52.4 | 126.3 | 128.1 |
| 136.0 | 81.0 | 180.0 | 33.4 | 121.8 | 130.4 |
| 138.0 | 112.0 | 242.4 | 14.4 | 137.7 | 205.6 |
| 139.0 | 297.0 | 205.2 | 25.2 | 122.2 | 120.6 |
| 140.0 | 234.5 | 187.9 | 25.2 | 120.1 | 115.8 |
| 141.0 | 295.5 | 234.2 | 30.3 | 147.0 | 144.8 |
| 142.0 | 230.5 | 334.9 | 36.8 | 248.9 | 252.0 |
| 143.0 | 145.0 | 242.4 | 39.3 | 158.2 | 174.2 |

TABLE 3-continued

AVERAGE DATA FOR EVERY SAMPLE
(LDL CORRELATION)

| Sample no | TG mg/dl | TC mg/dl | HDL mg/dl | LDL mg/dl | LDL-CAL. mg/dl |
|---|---|---|---|---|---|
| 144.0 | 180.0 | 254.6 | 46.5 | 195.7 | 172.1 |
| 145.0 | 143.0 | 137.0 | 34.4 | 94.8 | 74.0 |
| 146.0 | 277.0 | 136.5 | 11.3 | 89.6 | 69.8 |
| 147.0 | 243.0 | 127.7 | 15.4 | 78.3 | 63.7 |
| 148.0 | 64.0 | 162.3 | 44.2 | 115.4 | 105.4 |
| 149.0 | 218.5 | 249.5 | 41.1 | 178.3 | 164.7 |
| 150.0 | 92.0 | 164.0 | 41.5 | 98.3 | 104.1 |
| 151.0 | 106.0 | 164.1 | 46.2 | 113.0 | 96.7 |

TABLE 4

DATA NOT INCLUDED IN LDL CORRELATION
10 Samples

| Sample no | TG mg/dl | TC mg/dl | HDL mg/dl | LDL mg/dl | LDL-CAL. mg/dl |
|---|---|---|---|---|---|
| 21.0 | 2400.0 | 354.3 | 77.2 | 204.4 | |
| 37.0 | 294.0 | 242.7 | | 160.2 | |
| 88.0 | 308.5 | 431.5 | 46.4 | 194.1 | 323.4 |
| 93.0 | 1390.0 | 291.8 | 16.3 | 94.5 | |
| 94.0 | 914.5 | 416.0 | 32.8 | 165.7 | |
| 98.0 | 417.0 | 144.9 | 19.8 | 94.9 | 41.7 |
| 123.0 | 368.5 | 389.3 | 18.3 | 138.0 | 297.3 |
| 126.0 | 797.5 | 297.6 | 26.7 | 125.6 | |
| 134.0 | 294.0 | 81.2 | 11.8 | 59.8 | 10.7 |
| 137.0 | 422.5 | 730.5 | 25.5 | 391.9 | 620.5 |

I claim:

1. A method for direct quantitative determination of LDL-cholesterol in a sample of blood plasma, which comprises:
   (a) applying a sample of blood plasma to particulate silica capable of selectively adsorbing the lipoproteins from a plasma sample;
   (b) incubating said silica in an incubation chamber having a water-saturated atmosphere;
   (c) separating the silica from the non-adsorbed components;
   (d) washing said silica with water;
   (e) incubating said silica in an appropriate detergent to remove HDL fraction;
   (f) separating said silica from the detergent;
   (g) extracting the LDL-cholesterol from said silica; and
   (h) determining the LDL-cholesterol with a clinical chemistry analyzer, or any spectrophotometer.

2. A method according to claim 1 wherein the particulate silica is fumed silica.

3. A method according to claim 1 wherein said silica is coated on a solid inert carrier.

4. A method according to claim 3 wherein the inert carrier is in the shape of a plate, rod or ball.

5. A method according to claim 4 wherein the inert carrier is glass, paper or plastic polymer.

6. A method according to claim 1 wherein the chemistry analyzer is an automated clinical chemistry analyzer.

7. A method according to claim 1 wherein the detergent solution for extracting the HDL fractions of lipoproteins from aid silica is Polyoxy ethylene (20) sorbitan monostearate.

8. A method according to claim 1 wherein the detergent solution for extracting the LDL fraction from said silica is Triton X-100 or Sodium dodecyl sulfate.

9. A method according to claim 1 which comprises:
   (a) applying a 5 μL sample of blood plasma to fumed silica coated on a plate or rod of a solid inert material;
   (b) incubating said silica for 10 minutes in an incubation chamber having a water-saturated atmosphere;
   (c) separating said silica from the non-adsorbed components;
   (d) rinsing said silica with tap water;
   (e) incubating said silica for 20 minutes at 37° C. in 750 μL of the appropriate detergent to remove the HDL fraction;
   (f) separating said silica from the detergent;
   (g) extracting LDL-cholesterol by incubating said silica for 15 minutes at 37° C. in the appropriate detergent;
   (h) determining the optical density at 500 nm; and
   (i) calculating the concentration of LDL-cholesterol with respect to the appropriate standard.

10. A method according to claim 9 wherein the detergent used in step (e) is polyoxy ethylene (20) sorbitan mono stearate.

11. A method according to claim 9 wherein the detergent used in step (g) is Triton X-100 or Sodium dodecyl sulfate.

12. A method according to claim 9 wherein the determination of LDL-cholesterol comprises:
   (a) adding 0.4 mL of cholesterol reagent to 100 μL of the extraction solution;
   (b) incubating for 10 minutes;
   (c) determining the optical density at 500 nm; and
   (d) calculating the concentration of LDL-cholesterol with respect to the appropriate standard.

* * * * *